(12) United States Patent
Nichols et al.

(10) Patent No.: US 7,077,130 B2
(45) Date of Patent: *Jul. 18, 2006

(54) DISPOSABLE INHALER SYSTEM

(75) Inventors: Walter A. Nichols, Chesterfield, VA (US); F. Murphy Sprinkel, Jr., Glen Allen, VA (US)

(73) Assignee: Chrysalis Technologies Incorporated, Richmond, VA (US)

( * ) Notice: Subject to any disclaimer, the term of this patent is extended or adjusted under 35 U.S.C. 154(b) by 164 days.

This patent is subject to a terminal disclaimer.

(21) Appl. No.: 10/005,155

(22) Filed: Dec. 7, 2001

(65) Prior Publication Data

US 2002/0078951 A1 Jun. 27, 2002

Related U.S. Application Data

(63) Continuation-in-part of application No. 09/742,321, filed on Dec. 22, 2000.

(51) Int. Cl.
*A61M 16/00* (2006.01)

(52) U.S. Cl. .............................. 128/203.26; 128/203.12

(58) Field of Classification Search ............ 128/203.12, 128/203.14, 203.16, 203.17, 203.21, 203.26, 128/203.27, 203.28; 206/528, 531, 532, 538, 206/738
See application file for complete search history.

(56) References Cited

U.S. PATENT DOCUMENTS

| | | |
|---|---|---|
| 2,896,856 A | 7/1959 | Kravits |
| 3,084,698 A | 4/1963 | Smith |
| 3,157,179 A | 11/1964 | Paullus et al. |
| 3,162,324 A | 12/1964 | Houser |

(Continued)

FOREIGN PATENT DOCUMENTS

| | | |
|---|---|---|
| BE | 354004 A | 9/1928 |
| BE | 354094 A | 9/1928 |
| DE | 1036470 B1 | 8/1958 |
| EP | 0358114 A | 3/1990 |
| EP | 0642802 A2 | 5/1996 |
| FR | 667979 A | 10/1929 |
| HU | 168128 B | 11/1977 |
| HU | 216121 B | 3/1991 |
| HU | 207457 A | 4/1993 |
| HU | P953409 | 6/1994 |
| WO | 94/09842 A | 5/1994 |
| WO | 98/17131 | 4/1998 |

OTHER PUBLICATIONS

Barry, P.W. et al. "In Vitro Comparison of the Amount of Salbutamol Available for Inhalation From Different Formulations Used with Different Spacer Devices" Eur Respir J 1997; 10: 1345–1348.

(Continued)

*Primary Examiner*—Henry Bennett
*Assistant Examiner*—Joseph Weiss
(74) *Attorney, Agent, or Firm*—Burns, Doane, Swecker & Mathis, LLP

(57) ABSTRACT

A disposable aerosol generator for use with an inhaler device which includes a heater adapted to volatilize fluid stored in the disposable aerosol generator and method of using the inhaler. The disposable body includes a sealed chamber and an outlet, the chamber being located between first and second layers of material. The chamber holds a predetermined volume of a fluid which is expelled through the outlet when the fluid in the chamber is volatilized by the heater. The disposable body can include a series of spaced apart aerosol generators, each of which can be advanced to a release position at which the heater can heat one of the fluid containing chambers. Prior to heating the fluid, the outlet can be formed by severing the first and/or second layer with a piercing element and the volatilized fluid can be expelled from the outlet into a passage of a dispensing member.

39 Claims, 4 Drawing Sheets

U.S. PATENT DOCUMENTS

| | | | |
|---|---|---|---|
| 3,431,393 A | 3/1969 | Katsuda | |
| 3,486,663 A | 12/1969 | Humphrey | |
| 3,658,059 A | 4/1972 | Steil | |
| 3,716,416 A | 2/1973 | Adlhart et al. | |
| 3,750,961 A | 8/1973 | Franz | |
| 3,847,304 A | 11/1974 | Cohen | |
| 3,859,398 A | 1/1975 | Havstad | |
| 3,902,635 A | 9/1975 | Jinotti | |
| 3,903,883 A | 9/1975 | Pecina et al. | |
| 3,904,083 A | 9/1975 | Little | |
| 3,967,001 A | 6/1976 | Almaula et al. | |
| 3,987,941 A | 10/1976 | Blessing | |
| 3,993,246 A | 11/1976 | Erb et al. | |
| 3,995,371 A | 12/1976 | O'Keefe | |
| 4,012,471 A | 3/1977 | Kunkle, Jr. | |
| 4,012,472 A | 3/1977 | Lindsey | |
| 4,012,473 A | 3/1977 | Lindsey et al. | |
| 4,042,153 A | 8/1977 | Callahan et al. | |
| 4,060,082 A | 11/1977 | Lindberg et al. | |
| 4,077,542 A | 3/1978 | Petterson | |
| 4,161,282 A | 7/1979 | Erb et al. | |
| 4,162,501 A | 7/1979 | Mitchell et al. | |
| 4,215,708 A | 8/1980 | Bron | |
| 4,231,492 A | 11/1980 | Rios | |
| 4,258,073 A | 3/1981 | Payne | |
| 4,259,409 A | 3/1981 | Arnold | |
| 4,261,356 A | 4/1981 | Turner et al. | |
| 4,289,003 A | 9/1981 | Yang | |
| 4,291,838 A | 9/1981 | Williams | |
| 4,303,083 A | 12/1981 | Burruss, Jr. | |
| 4,383,171 A | 5/1983 | Sinha et al. | |
| 4,391,308 A | 7/1983 | Steiner | |
| 4,395,303 A | 7/1983 | Weir | |
| 4,433,797 A | 2/1984 | Galia | |
| 4,471,892 A | 9/1984 | Coleman | |
| 4,512,341 A | 4/1985 | Lester | |
| 4,575,609 A | 3/1986 | Fassel et al. | |
| 4,627,432 A | 12/1986 | Newell et al. | |
| 4,649,911 A | 3/1987 | Knight et al. | |
| 4,682,010 A | 7/1987 | Drapeau et al. | |
| 4,695,625 A | 9/1987 | Macdonald | |
| 4,700,657 A | 10/1987 | Butland | |
| 4,730,111 A | 3/1988 | Vestal et al. | |
| 4,735,217 A | 4/1988 | Gerth et al. | |
| 4,744,932 A | 5/1988 | Browne | |
| 4,749,778 A | 6/1988 | Fukuzawa et al. | |
| 4,753,352 A * | 6/1988 | Dauphin et al. | 206/538 |
| 4,762,995 A | 8/1988 | Browner et al. | |
| 4,776,515 A | 10/1988 | Michalchik | |
| 4,790,305 A | 12/1988 | Zoltan et al. | |
| 4,811,731 A | 3/1989 | Newell et al. | |
| 4,819,625 A | 4/1989 | Howe | |
| 4,819,834 A | 4/1989 | Thiel | |
| 4,829,996 A | 5/1989 | Noakes et al. | |
| 4,837,260 A | 6/1989 | Sato et al. | |
| 4,848,374 A | 7/1989 | Chard et al. | |
| 4,864,044 A | 9/1989 | Lewis et al. | |
| 4,871,115 A | 10/1989 | Hessey | |
| 4,871,623 A | 10/1989 | Hoopman et al. | |
| 4,877,989 A | 10/1989 | Drews et al. | |
| 4,911,157 A | 3/1990 | Miller | |
| 4,922,901 A | 5/1990 | Brooks et al. | |
| 4,926,852 A | 5/1990 | Zoltan et al. | |
| 4,935,624 A | 6/1990 | Henion et al. | |
| 4,941,483 A | 7/1990 | Ridings et al. | |
| 4,947,875 A | 8/1990 | Brooks et al. | |
| 4,974,754 A | 12/1990 | Wirz | |
| 4,982,097 A | 1/1991 | Slivon et al. | |
| 4,992,206 A | 2/1991 | Waldron | |
| 5,021,802 A | 6/1991 | Allred | |
| 5,044,565 A | 9/1991 | Alexander | |
| 5,056,511 A | 10/1991 | Ronge | |
| 5,060,671 A | 10/1991 | Counts et al. | |
| 5,063,921 A | 11/1991 | Howe | |
| 5,096,092 A | 3/1992 | Devine | |
| 5,115,911 A * | 5/1992 | Schulte et al. | 206/330 |
| 5,125,441 A | 6/1992 | Mette | |
| 5,133,343 A | 7/1992 | Johnson, IV et al. | |
| 5,134,993 A | 8/1992 | van der Linden et al. | |
| 5,135,009 A | 8/1992 | Müller et al. | |
| 5,144,962 A | 9/1992 | Counts et al. | |
| 5,151,827 A | 9/1992 | Ven et al. | |
| 5,178,305 A | 1/1993 | Keller | |
| 5,184,776 A | 2/1993 | Minier | |
| 5,217,004 A | 6/1993 | Blasnik et al. | |
| 5,226,441 A | 7/1993 | Dunmire et al. | |
| 5,228,444 A | 7/1993 | Burch | |
| 5,230,445 A | 7/1993 | Rusnak | |
| 5,231,983 A | 8/1993 | Matson et al. | |
| 5,259,370 A | 11/1993 | Howe | |
| 5,290,540 A | 3/1994 | Prince et al. | |
| 5,298,744 A | 3/1994 | Mimura et al. | |
| 5,299,565 A | 4/1994 | Brown | |
| 5,322,057 A | 6/1994 | Raabe et al. | |
| 5,327,915 A | 7/1994 | Porenski et al. | |
| 5,342,180 A | 8/1994 | Daoud | |
| 5,342,645 A | 8/1994 | Eisele et al. | |
| 5,349,946 A | 9/1994 | McComb | |
| 5,395,445 A | 3/1995 | Bohanan | |
| 5,421,489 A | 6/1995 | Holzner, Sr. et al. | |
| 5,462,597 A | 10/1995 | Jubran | |
| 5,474,059 A | 12/1995 | Cooper | |
| 5,509,557 A | 4/1996 | Jimarez et al. | |
| 5,515,842 A | 5/1996 | Ramseyer et al. | |
| 5,522,385 A | 6/1996 | Lloyd et al. | |
| 5,556,964 A | 9/1996 | Hofstraat et al. | |
| 5,564,442 A | 10/1996 | MacDonald et al. | |
| 5,565,677 A | 10/1996 | Wexler | |
| 5,575,929 A | 11/1996 | Yu et al. | |
| 5,585,045 A | 12/1996 | Heinonen et al. | |
| 5,611,846 A | 3/1997 | Overton et al. | |
| 5,617,844 A | 4/1997 | King | |
| 5,622,166 A | 4/1997 | Eisele et al. | |
| 5,642,728 A | 7/1997 | Andersson et al. | |
| 5,674,860 A | 10/1997 | Carling et al. | |
| 5,682,874 A | 11/1997 | Grabenkort et al. | |
| 5,730,158 A | 3/1998 | Collins et al. | |
| 5,743,250 A | 4/1998 | Gonda et al. | |
| 5,743,251 A * | 4/1998 | Howell et al. | 128/200.14 |
| 5,756,995 A | 5/1998 | Maswadeh et al. | |
| 5,765,724 A | 6/1998 | Amberg et al. | |
| 5,792,422 A * | 8/1998 | Lin et al. | 422/31 |
| 5,823,178 A | 10/1998 | Lloyd et al. | |
| 5,839,430 A | 11/1998 | Cama | |
| 5,855,202 A | 1/1999 | Andrade | |
| 5,856,671 A | 1/1999 | Henion et al. | |
| 5,863,652 A | 1/1999 | Matsumura et al. | |
| 5,869,133 A | 2/1999 | Anthony et al. | |
| 5,872,010 A | 2/1999 | Karger et al. | |
| 5,875,776 A | 3/1999 | Vaghefi | |
| 5,878,752 A | 3/1999 | Adams et al. | |
| 5,881,714 A | 3/1999 | Yokoi et al. | |
| 5,906,202 A | 5/1999 | Schuster et al. | |
| 5,914,122 A | 6/1999 | Otterbeck et al. | |
| 5,932,249 A | 8/1999 | Gruber et al. | |
| 5,932,315 A | 8/1999 | Lum et al. | |
| 5,934,099 A * | 8/1999 | Cook et al. | 62/457.2 |
| 5,934,272 A | 8/1999 | Lloyd et al. | |
| 5,934,273 A | 8/1999 | Andersson et al. | |
| 5,944,025 A | 8/1999 | Cook et al. | |
| 5,954,979 A | 9/1999 | Counts et al. | |

| | | | |
|---|---|---|---|
| 5,957,124 A | 9/1999 | Lloyd et al. | |
| 5,970,973 A | 10/1999 | Gonda et al. | |
| 5,970,974 A | 10/1999 | Van Der Linden et al. | |
| 5,978,548 A | 11/1999 | Holmstrand et al. | |
| 5,993,633 A | 11/1999 | Smith et al. | |
| 6,014,970 A | 1/2000 | Ivri et al. | |
| 6,020,575 A * | 2/2000 | Nagle et al. | 219/432 |
| 6,028,293 A * | 2/2000 | Nagle et al. | 219/432 |
| 6,053,176 A * | 4/2000 | Adams et al. | 131/329 |
| 6,054,032 A | 4/2000 | Haddad et al. | |
| 6,069,214 A | 5/2000 | McCormick et al. | |
| 6,069,219 A | 5/2000 | McCormick et al. | |
| 6,070,575 A | 6/2000 | Gonda et al. | |
| 6,071,428 A | 6/2000 | Franks et al. | |
| 6,071,554 A | 6/2000 | Isomura et al. | |
| 6,076,522 A | 6/2000 | Dwivedi et al. | |
| 6,077,543 A | 6/2000 | Gordon et al. | |
| 6,080,721 A | 6/2000 | Patton | |
| 6,085,740 A | 7/2000 | Ivri et al. | |
| 6,085,753 A | 7/2000 | Gonda et al. | |
| 6,089,228 A | 7/2000 | Smith et al. | |
| 6,095,153 A | 8/2000 | Kessler et al. | |
| 6,098,615 A | 8/2000 | Lloyd et al. | |
| 6,098,620 A | 8/2000 | Lloyd et al. | |
| 6,103,270 A | 8/2000 | Johnson et al. | |
| 6,116,238 A * | 9/2000 | Jackson et al. | 128/203.15 |
| 6,116,516 A | 9/2000 | Gañán-Calvo | |
| 6,116,893 A | 9/2000 | Peach | |
| 6,119,953 A | 9/2000 | Gañán-Calvo et al. | |
| 6,123,068 A | 9/2000 | Lloyd et al. | |
| 6,123,936 A | 9/2000 | Platz et al. | |
| 6,131,567 A | 10/2000 | Gonda et al. | |
| 6,131,570 A * | 10/2000 | Schuster et al. | 128/203.26 |
| 6,136,346 A | 10/2000 | Eljamal et al. | |
| 6,138,668 A | 10/2000 | Patton et al. | |
| 6,155,268 A | 12/2000 | Takeuchi | |
| 6,158,431 A | 12/2000 | Poole | |
| 6,158,676 A | 12/2000 | Hughes | |
| 6,159,188 A | 12/2000 | Laibovitz et al. | |
| 6,164,630 A | 12/2000 | Birdsell et al. | |
| 6,165,463 A | 12/2000 | Platz et al. | |
| 6,167,880 B1 | 1/2001 | Gonda et al. | |
| 6,174,469 B1 | 1/2001 | Gañán-Calvo | |
| 6,182,712 B1 | 2/2001 | Stout et al. | |
| 6,187,214 B1 | 2/2001 | Gañán-Calvo | |
| 6,187,344 B1 | 2/2001 | Eljamal et al. | |
| 6,189,803 B1 | 2/2001 | Gañán-Calvo | |
| 6,192,882 B1 | 2/2001 | Gonda | |
| 6,197,835 B1 | 3/2001 | Gañán-Calvo | |
| 6,205,999 B1 | 3/2001 | Ivri et al. | |
| 6,206,242 B1 | 3/2001 | Amberg et al. | |
| 6,207,135 B1 | 3/2001 | Rössling et al. | |
| 6,223,746 B1 | 5/2001 | Jewett et al. | |
| 6,230,706 B1 | 5/2001 | Gonda et al. | |
| 6,231,851 B1 | 5/2001 | Platz et al. | |
| 6,234,167 B1 | 5/2001 | Cox et al. | |
| 6,234,402 B1 | 5/2001 | Gañán-Calvo | |
| 6,235,177 B1 | 5/2001 | Borland et al. | |
| 6,250,298 B1 | 6/2001 | Gonda et al. | |
| 6,250,301 B1 * | 6/2001 | Pate | 128/203.26 |
| 6,257,233 B1 | 7/2001 | Burr et al. | |
| 6,258,341 B1 | 7/2001 | Foster et al. | |
| 6,263,872 B1 | 7/2001 | Schuster et al. | |
| 6,267,155 B1 | 7/2001 | Parks et al. | |
| 6,275,650 B1 | 8/2001 | Lambert | |
| 6,276,347 B1 | 8/2001 | Hunt | |
| 6,284,525 B1 | 9/2001 | Mathies et al. | |
| 6,288,360 B1 | 9/2001 | Beste | |
| 6,290,685 B1 | 9/2001 | Insley et al. | |
| 6,294,204 B1 | 9/2001 | Rössling et al. | |
| 6,295,986 B1 | 10/2001 | Patel et al. | |
| 6,318,361 B1 | 11/2001 | Sosiak | |
| 6,367,473 B1 * | 4/2002 | Kafer | 128/203.21 |
| 6,378,518 B1 * | 4/2002 | Miekka et al. | 128/203.15 |
| 6,481,437 B1 * | 11/2002 | Pate | 128/203.26 |

OTHER PUBLICATIONS

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477–7505, May–Jun. 1994.

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp 97–102.

Hou, Shuguang et al. Solution Stability of Budenosonide in Novel Aerosol Formulations Abstract No. 2582, Solid State Physical Pharmacy, Nov. 17, 1998, p. S–307.

Kousaka, Yasuo et al., "Generation of Aerosol Particles by Boiling of Suspensions", Aerosol Science and Technology, 21:236–240 (1994).

Morén, Folke "Drug Deposition of Pressurized Inhalation Aerosols I. Influence of Actuator Tube Design" AB Draco (Subsidiary of AB Astra, Sweden) Research and Development Laboratories Pack, S–221 01 Lund (Sweden), International Journal of Pharmaceutrics, 1 (1978) 205–212.

Newman, Stephen P. et al. "Deposition of Pressurized Suspension Aerosols Inhaled Through Extension Devices[1–3]" Am Rev Respir Dis 1981; 124:317–320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766–770, Jul. 1980.

Notification of Transmittal of the International Search Report or the Declaration for PCT/US01/44809 dated May 8, 2003.

Notification of Transmittal of the International Search Report or the Declaration dated Mar. 6, 2003 for PCT/US02/38910.

Written Opinion dated Nov. 4, 2003 for PCT/US/44809.

Written Opinion dated Dec. 24, 2003 for PCT/US02/38910.

* cited by examiner

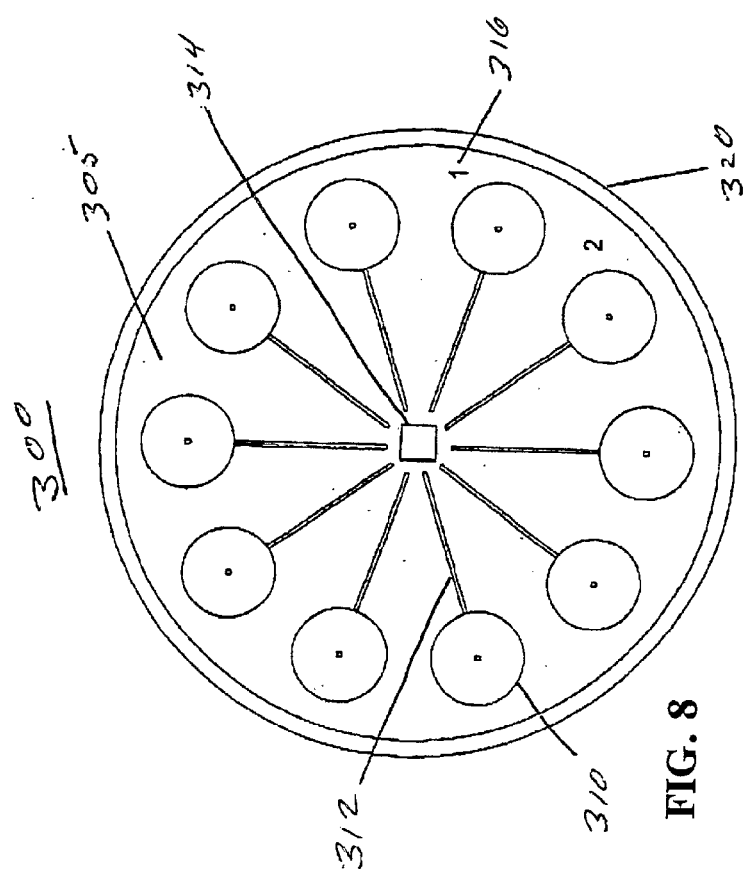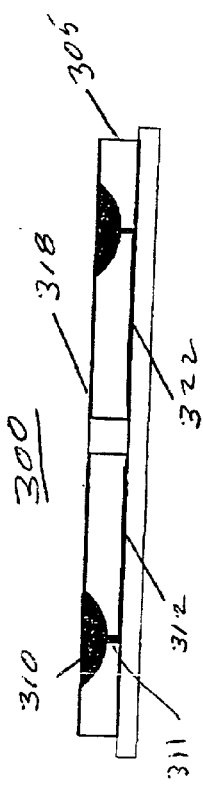
FIG. 8
FIG. 9

DISPOSABLE INHALER SYSTEM

RELATED PATENT APPLICATIONS

This is a Continuation-in-Part Application of Ser. No. 09/742,321, filed Dec. 22, 2000.

BACKGROUND OF THE INVENTION

1. Field of the Invention

The present invention relates to an apparatus, system and methods of administering a fluid such as a medicated fluid in metered amount such as a unit dose to treat respiratory ailments. In particular, the invention relates to disposable aerosol generators, wherein the aerosols are generated via vaporization.

2. Description of Related Art

Aerosols are useful in a variety of applications including treatment of respiratory ailments. Various techniques for generating aerosols are disclosed in U.S. Pat. Nos. 4,811,731; 4,627,432; 5,743,251; and 5,823,178.

In particular, two distinct methods for delivery of medicated fluid in the form of an aerosol have been developed. In accordance with one method, a pharmaceutically active drug is dispensed in a low boiling point propellant (e.g., chloro-fluoro-carbon (CFC) or (HFA)) loaded in a pressurized canister from which the drug/propellant formulation may be released by the use of a device generally known as a metered dose inhaler. Once released the propellant evaporates and particles of the drug are inhaled by the patient. The other method involves the use of a nebulizer which creates an inhalable mist of fine particles from a solution or suspension of a drug. Both methods are hindered by significant problems relating to administering the proper dose.

In drug delivery applications, it is typically desirable to provide an aerosol having average mass median particles diameter of less than 2 microns to facilitate deep lung penetration. Additionally, it is desirable, in certain drug applications, to deliver medicaments at high flow rates (i.e., above 1 milligram per second). Devices for controlling the flow rate of an aerosol are known. For example, U.S. Pat. No. 4,790,305 concerns controlling the particle size of a metered dose of aerosol for delivery to the walls of bronchi and bronchioles by filling a first chamber with medication and a second chamber with air such that all of the air is inhaled prior to the inhaling medication, and using flow control orifices to control the flow rate. U.S. Pat. No. 4,926,852 relates to metering a dose of medication into a flow-through chamber that has orifices to limit the flow rate to control particle size. U.S. Pat. No. 3,658,059 discloses a baffle that changes the size of an aperture in the passage of the suspension being inhaled to select the quantity and size of particles delivered. A problem associated with these devices is that they process the aerosol after it is generated and are inefficient and wasteful.

To meet the requirements of administering a fluid in the form of an aerosol and to overcome the disadvantages of the prior art, it is an object of the present invention to provide an aerosol generator which vaporizes the fluid at a controlled flow rate regardless of the fluid's viscosity.

It is another object of the invention to obtain uniform vaporization of the fluid that is expelled from the aerosol generator.

It is an object of the invention to provide a disposable aerosol generator which can deliver a metered dose of the fluid. By delivering individual single doses of medicated fluid it is possible to avoid contamination of the fluid, thereby negating the need for bacteriostatic compounds within the drug formulation.

It is a further object of the invention to provide a disposable cartridge which can incorporate a package having therein multiple disposable aerosol generators, each of which provides a single shot delivery, as required by the user.

It is yet another object of the invention to provide an inhaler device useable with a disposable cartridge that includes a mechanism for forcing a dose of medication from the disposable cartridge at a uniform rate of flow.

Other objects and aspects of the present invention will become apparent to one of ordinary skill in the art upon review of the specification, drawings and claims appended hereto.

SUMMARY OF THE INVENTION

According to one aspect of the invention, a disposable aerosol generator is provided which is adapted for use with an inhaler device which includes a heater arranged to volatilize fluid stored in the disposable aerosol generator. The aerosol generator comprises a disposable body having a sealed chamber and an outlet wherein first and second layers of material define the chamber. The chamber accommodates a predetermined volume of a fluid which is expelled through the outlet when the fluid in the chamber is volatilized by the heater.

According to another aspect of the invention, an inhaler device is provided which is usable with the disposable aerosol generator mentioned above, the inhaler device including a heater arranged to heat the fluid in the chamber so as to expel volatilized fluid from the outlet. The heater can comprise a layer of resistance heating material on a substrate which includes an opening located adjacent the outlet. In order to form the outlet, an opening device such as a piercing element can be provided which is adapted to pierce the first and/or second layer to form the outlet.

According to another aspect of the invention, a method of using the inhaler device mentioned above is provided, the method including severing the first and/or second layer so as to form the outlet and activating the heater so as to volatilize the fluid in the chamber and expel the volatilized fluid through the outlet.

According to a preferred method, the disposable body includes a series of spaced apart aerosol generators and the method includes moving the disposable body relative to the inhaler device so as to locate a first one of the aerosol generators at a position where the heater can heat the fluid in the chamber of the first aerosol generator and volatilize the fluid therein. The severing can be carried out by driving a piercing member through the first and/or second layer and the outlet can be located adjacent a passage of a dispensing member such that the volatilized fluid formed by the heater is expelled into the passage after passing through the outlet.

BRIEF DESCRIPTION OF THE DRAWINGS

The objects and advantages of the invention will become apparent from the following detailed description of the preferred embodiments thereof in connection with the accompanying drawing, in which:

FIGS. 8 and 9 show a disposable cartridge usable in the inhaler device of FIG. 7.

DETAILED DESCRIPTION OF THE PREFERRED EMBODIMENTS OF THE INVENTION

The present invention provides an inhaler effective for administering a fluid such as a medicated fluid in aerosol form. It has surprisingly and unexpectedly been determined that a metered amount of fluid can be delivered from the inhaler via a disposable aerosol generator wherein the fluid is fully vaporized and delivered at a predetermined flow rate.

Figure 1:
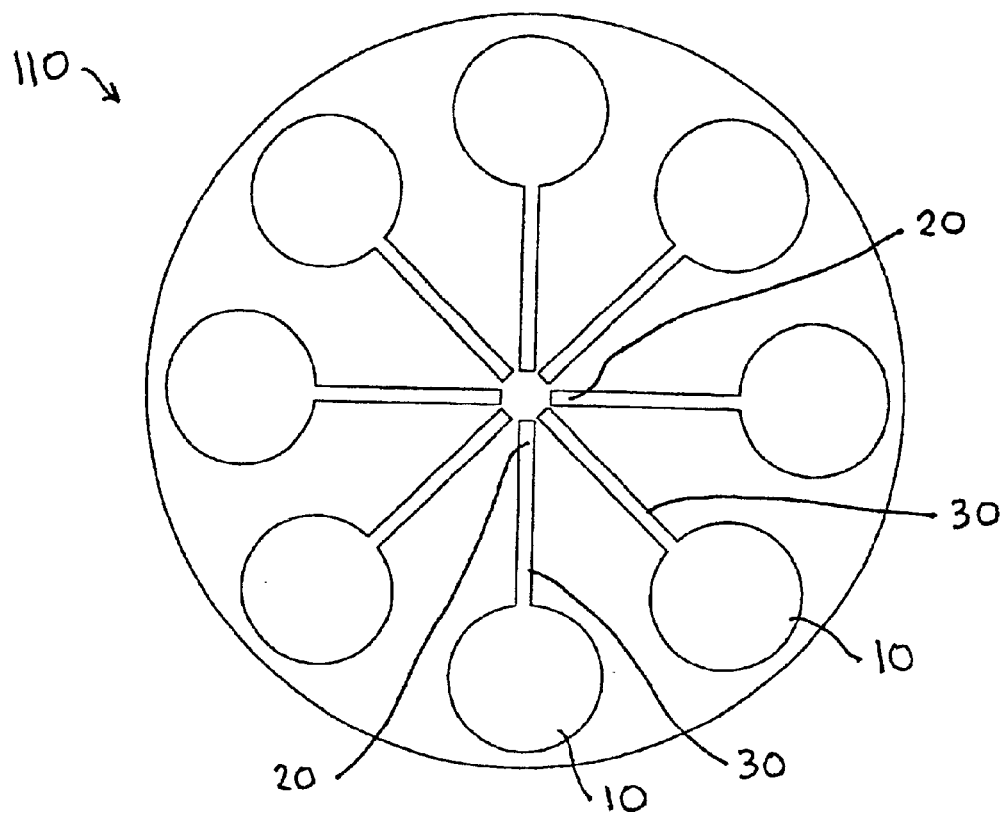
FIGS. 1 and 2 show details of a disposable body containing a series of aerosol generators according to one embodiment of the invention, FIG. 1 showing a top view thereof and FIG. 2 showing a side view thereof.
Figure 2:
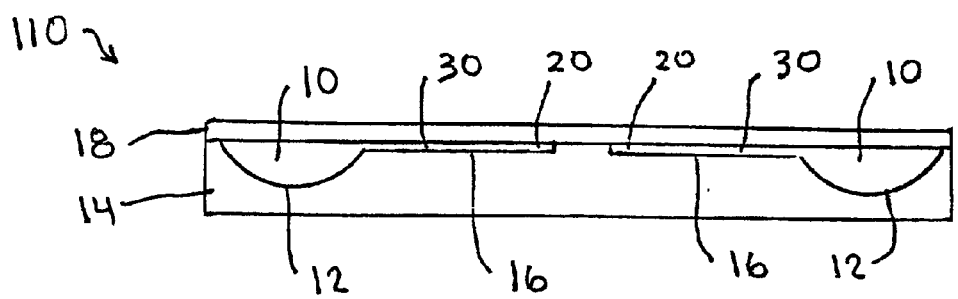
Figure 3:
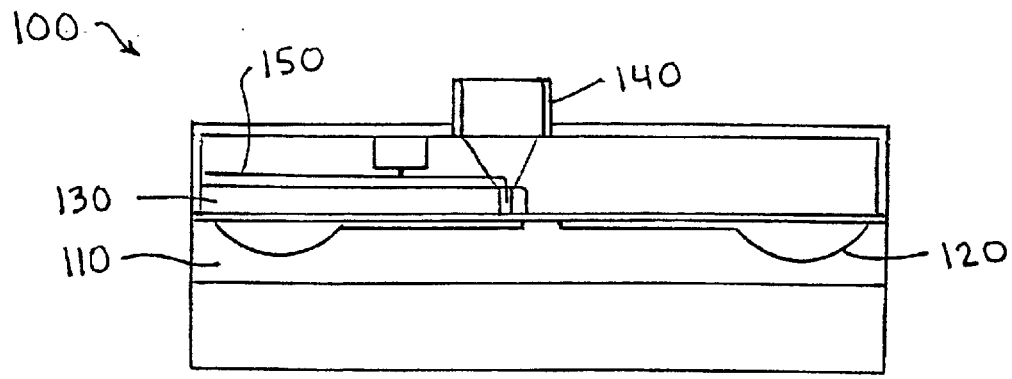
FIG. 3 shows an inhaler device according to an embodiment of the invention.
Figure 4:
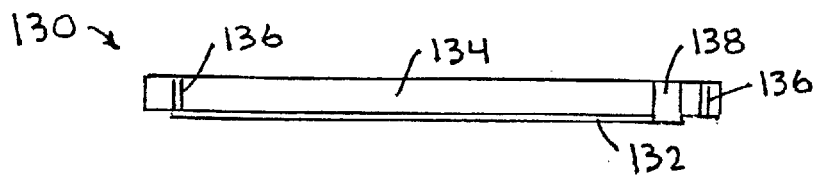
FIG. 4 shows details of a heater of the inhaler device shown in FIG. 3.

With reference to FIGS. 1 and 2, an aerosol generator in accordance with one embodiment of the present invention is shown schematically. A single shot chamber or reservoir 10 is designed to accommodate a predetermined volume of fluid which can incorporate a medicament for treating various respiratory ailments (e.g., a partial list includes albuterol, isoproterenol sulfate, metaproterenol sulfate, terbutaline sulfate, pirbuterol acetate, salmeterol xinotoate, formotorol; steroids including beclomethasone dipropionate, flunisolide, fluticasone, budesonide and triamcinolone acetonide, beclomethasone dipropionate, triamcinolone acetonide, flunisolide and fluticasone, etc.). Of course, the volume and composition of fluid may be predicated on the amount desired to treat a particular medical ailment.

An outlet 20 is in fluid communication with the chamber 10 and a heating member (not shown) disposed on or in proximate location to either chamber 10 and/or outlet 20 is operable to vaporize the fluid in the chamber 10 and eject the vaporized fluid out of the outlet 20. For instance, a heating member may be employed in conjunction with both the chamber 10 and outlet 20. In a preferred embodiment, the heater comprises part of a reusable inhaler device. However, the heater can be incorporated in the disposable body, e.g., a resistance heating element heated by passing current therethrough or by inductively heating the heating element.

In accordance with a preferred embodiment of the invention, chamber 10 is constructed from a material (e.g., polymeric, aluminum foil) resistant to heating. For example, in the embodiment shown in FIGS. 1 and 2, the chamber 10 is formed as a recess 12 in an injection molded body 14 of polymer material and a flow passage 30 comprises a channel 16 in the body 14, the channel 16 extending from the recess 12. The chamber 10 is sealed by a layer 18 such as aluminum foil heat sealed to the plastic body 14.

In order to provide multiple doses of medicated fluid in a disposable part of an inhaler, the plastic body 14 can include a plurality of recesses 12. The laminate thus described is capable of withstanding the pressure applied to the interior of the chamber through the application of heat necessary to vaporize the fluid contained therein. Outlet 20 is preferably a small aperture at the end of the flow passage 30, the outlet being initially closed to the atmosphere. The flow passage 30 can have any suitable size which is effective to expel the vaporized fluid into the atmosphere and form the aerosol of desired droplet size. For instance, flow passage 30 can have an inside diameter of about 0.05 to about 0.60 millimeter, preferably about 0.2 mm and a length of about 50 to 200 times the inside diameter. The chamber 10 can have any desired size such as a size suitable to deliver a single dose of medicated fluid, e.g., 5 μl.

In operation, the fluid in the chamber 10 is heated by a heating device which heats the fluid to a temperature sufficient to volatilize the fluid. In the case of an organic liquid material, the heating device preferably heats the fluid to approximately the boiling point, and preferably does not heat the fluid above 400° C., as most organic fluids are not stable when they are exposed to temperatures above 400° C.

Heating can be achieved in various ways including resistance or induction heating to heat the fluid via thermal conduction. Suitable heating devices envisioned for employment in the aerosol generator of the present invention include electrical resistance heaters, deposited resistance heating material such as thin platinum layers, electro-induction heating coils, etc. For example, the heating device can comprise an electrical resistance heater element arranged to thermally conduct heat into the chamber 10. The heater can be any suitable material such as platinum, tungsten, molybdenum or metal alloy such as an iron-based alloy having 71.7% (by weight) iron, 23% chromium, and 5.3% aluminum.

The flow passage 30 can have any desired configuration. For instance, the flow passage can have a uniform cross-sectional area along the length thereof between the chamber 10 and the outlet 20. However, the flow passage can vary in size along the length thereof, e.g., tapered so as to become more narrow in a direction towards the outlet 20. Further, the chamber need not comprise a concave circular recess but rather, can comprise any desired configuration sized to accommodate a single dose of the medicated fluid.

According to a preferred embodiment, the heater device can comprise a layer of resistance heating material deposited on the outside of a support member such as a plastic or ceramic member, e.g., alumina, glass, titania, zirconia, or yttria-stabilized zirconia which does not experience oxidation at normal operating temperatures.

The heater support and the heater layer preferably have a roughly matching coefficient of thermal expansion to minimize thermally induced delamination. Also, the ceramic support material can have a surface roughness to improve adhesion of the deposited heater layer. Platinum is desirable as a heater material in that it is resistant to oxidation degradation or other corrosion.

The heater layer can be deposited as a thin film on a ceramic support such that the heater layer has a thickness of, e.g., less than approximately 2 μm. The heater layer can be deposited onto the ceramic by any suitable method such as DC magnetron sputter deposition, e.g., using an HRC magnetron sputter deposition unit, in argon at $8.0 \times 10^{-3}$ Torr. Alternatively, other conventional techniques such as vacuum evaporation, chemical deposition, electroless plating, electroplating, and chemical vapor deposition can be employed to apply the heater layer to the substrate. It will be appreciated by those skilled in the art, that the energy produced by the heating device can be distributed optimally by tailoring the pattern of the thin film. For example, the heater pattern can be arranged to provide more heat near the outlet 20 than in the vicinity of the recess 12.

The closed end of the flow passage 20 can be opened by an opening device such as solenoid activated puncturing element. Alternatively, a cutting blade or scissors suitable for cutting the material sealing the flow passage 30 can be used to expel the volatilized fluid. It is further within the scope of the invention that other techniques such as a breakable seal can be employed on the closed end of the flow passage. The volatilized fluid can be expelled in a controlled manner taking into account properties of the fluid and the amount of heat needed to vaporize the fluid. The volatilized fluid can be expelled from the outlet 20 at a high velocity, e.g., approximately 90 m/s, but the volatilized fluid can be quickly dissipated in the atmosphere as the aerosol is formed from the condensing vapor, e.g., within about 2 mm of the outlet 20. The volatilized fluid can be mixed with ambient air in an inhaler mouthpiece surrounding the outlet 20, whereupon rapid cooling and condensation of the vapor result in formation of the aerosol.

The characteristics of the aerosol generated in accordance with the invention is a function of various parameters of the generator and the fluid provided. For aerosols intended for inhalation, for example, it is desirable for the aerosol to be approximately at body temperature when inhaled and for the mass median size of the aerosol to be less than 2 microns, preferably between 0.5 and 1 micron.

Upon delivery of the metered amount of fluid, in aerosol form, the aerosol generator comprising the chamber 10, outlet 20 and flow passage 30 can be discarded. In the case where multiple generators are provided in a multidose cartridge such as the disposable body shown in FIGS. 1 and 2, the cartridge can be disposed of when the last of the individual chambers have been emptied.

In accordance with another preferred embodiment, the heating device can comprise a plurality of heating members arranged to heat the fluid in the chamber and/or along the flow passage. Also, the fluid in the chamber could be expelled mechanically, e.g., by a member which pushes the fluid into the flow passage and a heater along the flow passage can be used to volatilize the fluid and expel the vaporized fluid out of the outlet 20.

With reference to FIGS. 3–6, a fluid delivery system is depicted, wherein individual disposable aerosol generators are transported to a fluid release position as required by the user. System 100 includes a cartridge 110 loaded with disposable aerosol generators 120. In a preferred embodiment, the aerosol generators 120 are provided in the form of packets, preferably constructed as described above in connection with FIGS. 1 and 2. A heating device 130 provides sufficient energy to each generator 120 to vaporize the fluid and expel the vaporized fluid through a passage in a dispenser 140. An opening device 150 can comprise a puncture element 150 activated by a solenoid 145, the puncture element 152 being operable by a suitable controller and circuitry to penetrate the layer 18 in the vicinity of outlet 20.

The heating device 130 includes an electrically resistive heating element 132 on a substrate 134, the heating element 132 being powered by electrically conductive connections 136 extending through vias in the substrate 134. The substrate 134 includes an opening 138 through which the piercing end of the puncture element 152 can move towards and away from the cartridge 110. In operation, the controller can be activated to operate the system 100 so as to rotate the cartridge 110 to a drug release position, actuate the solenoid to drive the puncture arm towards the cartridge so as to pierce the channel 16 and thereby form the outlet 20, and activate the heating element so as to heat the fluid in the chamber 10 whereby vaporized fluid is expelled through the dispenser 140.

Figure 5:
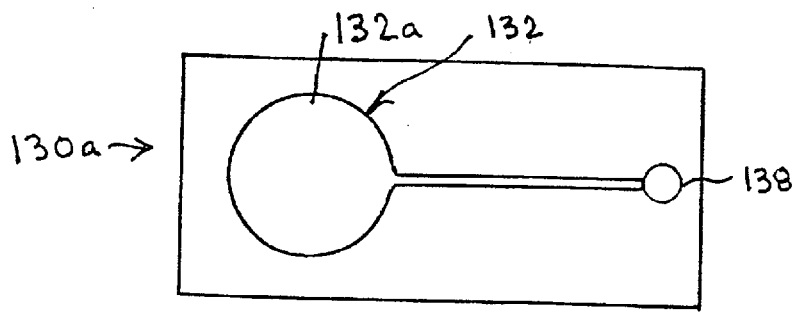
FIG. 5 shows details of a first heater pattern which can be used for a resistance heating layer in the heater shown in FIG. 4.
Figure 6:
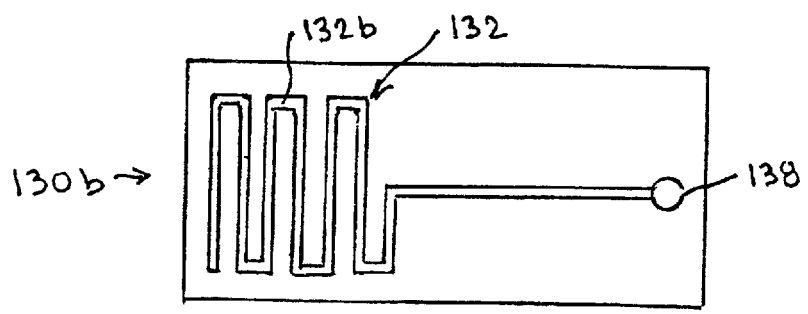
FIG. 6 shows details of a second heater pattern which can be used for a resistance heating layer in the heater shown in FIG. 4.

FIGS. 5 and 6 show embodiments of different heater patterns for the heater 130. The heater 130a shown in FIG. 5 includes a heating element 132a configured to completely cover the chamber 10 and flow passage 30. With the heater element pattern shown in FIG. 5, greater heating can be achieved in the flow passage 30 due to the smaller cross sectional area of the heating element along the flow passage. The heater 132b shown in FIG. 6 includes a heating element 132b configured as a sinusoidally shaped strip which overlies chamber 10 and a rectilinear strip which overlies the flow passage 20.

In operation, the disposable cartridge 110 can be loaded into the inhaler 100, and a transport mechanism (not shown) can be operated to successively transport the aerosol generators to the release position at which the heater volatilizes the fluid contained in the respective chamber. Driving power for the transport mechanism, the solenoid and the heating element can be provided by a power source such as a 9-volt battery. The dispenser 140 can be arranged to supply the vaporized fluid to a mouthpiece (not shown) of the inhaler 100.

Figure 7:
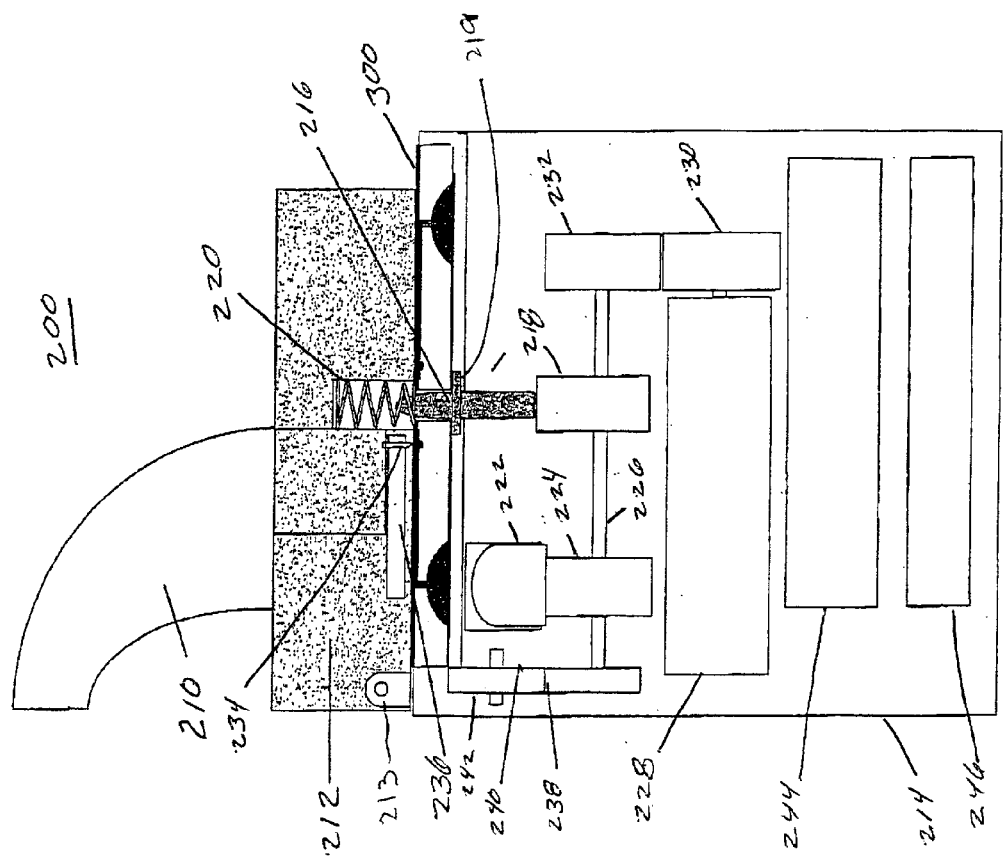
FIG. 7 shows an inhaler device according to another embodiment of the invention.

FIG. 7 shows an embodiment of an inhaler device having a disposable cartridge and modified piercing mechanism and FIGS. 8 and 9 show details of the disposable cartridge usable therein.

The inhaler device 200 of FIG. 7, includes a mouthpiece 210 connected to a hinged top portion 212 hingably connected to a main body 214 via hinge connection 213. The hinged top portion 212 can be pivoted open to load a disposable cartridge 300 in the device 200. After closing the top portion, it can be locked by a suitable mechanism (not shown).

The cartridge 300 rotates on a spindle 216. The spindle 216 is biased in contact with spindle cam 218 by spring 220 and the spindle cam 218 is driven in rotation by shaft 226. A piston 222 located below a reservoir discharging position is movable vertically by a cam 224 driven in rotation by shaft 226. A motor 228 drives a first gear 230 which in turn drives a second gear 232. The second gear 232 is connected to shaft 226 thereby causing rotation of shaft 226. As a result of rotation of shaft 226, spindle cam 218 lifts spindle 218 such that flange 219 on spindle 218 raises the cartridge 300. When the cartridge 300 is raised, puncture element 234 pierces an outlet in a flow passage 312 and piston 222 is pressed against a reservoir 310 in fluid communication with the flow passage 312 at a rate effective to cause liquid to flow into the flow passage 312 at a desired flow rate, e.g., a constant flow rate. The flow passage 312 is preferably of capillary size, e.g., a maximum width of 0.01 to 10 mm, preferably 0.05 to 1 mm, more preferably 0.1 to 0.5 mm. Alternatively, the capillary passage can be defined by transverse cross sectional area of the passage which can be $8 \times 10^{-5}$ to 80 mm$^2$, preferably $2 \times 10^{-3}$ to $8 \times 10^{-1}$ mm$^2$ and more preferably $8 \times 10^{-3}$ to $2 \times 10^{-1}$ mm$^2$.

During operation of the device 200, liquid in the flow passage 312 is vaporized and the vaporized liquid passes out of the pierced outlet so as to form an aerosol in the mouthpiece 210. To maximize heating of the flow passage, the flow passage 312 is held against heater 236 by the raised spindle 216. The heater can be activated prior to when the fluid is forced into the flow passage 312 by the piston 222.

After fluid in fluid reservoir 310 is forced out of the fluid reservoir 310 by piston 222, rotation of the shaft 226 causes the spindle cam 218 and the piston cam 224 to lower the spindle 216 and the piston 222. As the spindle 216 retracts, the disposable cartridge 300 is lowered into engagement with a drive mechanism for rotation of the cartridge. For example, a drive gear 238 driven by shaft 226 can be used to engage intermittent teeth 240 on gear 242 with gear teeth 320 on the rim of the disposable cartridge 300. Thus, rotation of shaft 226 causes disposable cartridge 300 to rotate to a position at which another fluid reservoir 310 of the disposable cartridge 300 is directly above piston 222.

Operation of the inhaler 200 can be controlled by a programmable controller 244. The controller 244 is preferably programmed to control operation of motor 228 and heater 236 as described above. The controller can be programmed to keep track of how many reservoirs have been dispensed and provide such information to a display (not shown). A switch and/or sensor such as a puff actuated sensor (not shown) can be used to detect a delivery condition indicating a user is ready to inhale the vaporized liquid. In response to the sensed condition, the controller 244 actuates the motor 228 and heating element 236. A battery 246, or other power source, can be used to provide power to the controller 244, motor 228 and heater 236.

FIGS. 8 and 9 depict a preferred embodiment of the disposable cartridge 300 usable in the inhaler device 200. The disposable cartridge 300 has a main body 305 in the shape of a disc that can be made of injection molded plastic. While a disc-shaped cartridge is preferred, the cartridge can have other configurations which include multiple reservoirs adapted to be indexed via rotation, linear movement or the like to a delivery position in an inhaler device.

The disposable cartridge 300 has a centrally located opening 314 which receives a free end of spindle 216. The opening 314 can be square as shown in FIG. 8 or have another configuration such as a circular opening. A plurality of fluid reservoirs 310 are circumferentially spaced around a lower surface of the body 305. Each of the fluid reservoirs 310 is in fluid communication via a passage 311 with a flow passage 312 on an upper surface of the cartridge and leading radially inwardly from the fluid reservoir 310 towards the centrally located opening 314. Gear teeth 320 are located on an outer portion of the disposable cartridge 300. The flow passages 312, fluid reservoirs 310 and gear teeth 320 can be molded in a one-piece polymer material.

The disposable cartridge 300 can include indicia 316 disposed proximate each of the fluid reservoirs 310. The indicia 316 can be a series of numbers representing each of the fluid reservoirs 310 in disposable cartridge 300. The indicia 316 can be printed, molded or attached in any suitable manner to the disposable cartridge 300. When the cartridge is loaded in the inhaler, the indicia 316 can be arranged to be visible to the user and provide information such as the remaining number of unused reservoirs available for inhalation.

To maintain the fluid in the reservoirs, the cartridge can include layers of material covering upper and lower surfaces thereof. For example, a film 318 can be used to cover the bottom surface of the cartridge, e.g., the film 318 can cover a single reservoir or all of the reservoirs by covering the entire lower surface of disposable cartridge 300. The film 318 is preferably made from polymer material and has a thickness of less than 0.007 inches. Another layer such as a foil 322 can be used to cover the flow passages 312 of the disposable cartridge 300. The foil 322 can cover an individual flow passage or the entire upper surface of disposable cartridge 300. The foil 322 is preferably aluminum foil having a thickness of less than 0.003 inches. An aluminum foil can be easily punctured by the piercing element 234 and is heat resistant so as to withstand the heat emanating from heating element 236.

While the invention has been described in detail with reference to specific embodiments thereof, it will be apparent to those skilled in the art that various changes and modifications can be made, and equivalents employed, without departing from the scope of the appended claims.

What is claimed is:

1. A disposable aerosol generator for use with an inhaler device which includes a heater adapted to volatilize liquid store in the disposable aerosol generator, comprising:

a disposable body comprising a disc including a series of spaced apart aerosol generators, each aerosol generator including a sealed chamber and an outlet which can be opened to expel vapor, the disposable body including first and second layers of material defining the chamber, the chamber accommodating a predetermined volume of a liquid which is expelled through the opened outlet as vapor when the liquid in the chamber is volatilized by the heater, the chamber of each respective aerosol generator being located adjacent an outer portion of the disc and the outlet of each respective aerosol generator being located adjacent a central portion of the disc.

2. The aerosol generator according to claim 1, wherein the outlet is located at an end of a flow passage located between the first and second layers of material.

3. The aerosol generator according to claim 2, wherein the flow passage comprises a rectilinear channel having a width of 0.01 to 10 mm and a length of at least 5 mm.

4. The aerosol generator according to claim 1, wherein the disposable body is configured to fit in the inhaler device so a to allow advancement of each respective aerosol generator to a release position at which the heater can heat the liquid in the chamber of the respective aerosol generator.

5. The aerosol generator according to claim 4, wherein each of the aerosol generators includes an outlet located at the end of a flow passage, the flow passage of each aerosol generator being located between the first and second layers.

6. The aerosol generator according to claim 1, wherein the first layer of material comprises an injection molded polymer material wherein the chamber comprises a recess in the polymer material.

7. The aerosol generator according to claim 1, wherein the first layer of material comprises a polymer material and the second layer of material comprises a foil layer heat sealed to the polymer layer.

8. The aerosol generator according to claim 7, wherein the outlet is located at an end of a flow passage extending from the chamber, the flow passage comprising a channel in the polymer layer.

9. An inhaler device usable with the disposable aerosol generator according to claim 1, wherein the inhaler device includes a heater arranged to heat the liquid in the chamber of a respective aerosol generator so as to expel vapor from the opened outlet.

10. The inhaler device according to claim 9, wherein the heater comprises an electrical resistance heater.

11. A method of forming an aerosol using the inhaler device according to claim 10, comprising severing at least one of the first layer and second layer so as to open the outlet of a respective aerosol generator and activating the heater so as to volatilize the liquid in the chamber and expel the vapor through the outlet.

12. The method according to claim 11, wherein the method including moving the disposable body relative to the inhaler device so as to locate a first one of the aerosol generators at a position where the heater can heat the liquid in the chamber of the first aerosol generator and volatilize the liquid therein.

13. The method according to claim 11, wherein the severing is carried out by driving a piercing member through at leas one of the first and second layer, the outlet being located adjacent a passage of a dispensing member and the vapor formed by the heater being expelled into the passage after passing through the opened outlet.

14. The method according to claim 13, wherein each of the aerosol generators includes a flow passage extending rectilinearly from the chamber, the heater including a first portion arranged to heat the chamber and a second portion arranged to heat the flow passage of a respective aerosol generator, the first and second portions of the heater comprising a layer of resistance heating material configured such that the second portion of the heater becomes hotter than the first portion of the heater during volatilization the liquid in the chamber.

15. A method of forming an aerosol using the inhaler device according to claim 11, wherein the chamber is located on a lower surface of the disposable body and the outlet is located on an upper surface of the disposable body, the outlet being connected to the chamber by a flow passage in the upper surface of the disposable body, the method including a step of mechanically forcing liquid out of the chamber so as to flow along the flow passage and activating the heater so as to volatilize the liquid in the flow passage and expel the vapor through the opened outlet.

16. The method according to claim 15, wherein the liquid is forced out of the chamber by pressing a piston against the disposable body.

17. The method according to claim 15, wherein the disposable body is movable vertically toward and away from the heater, the method including a step of moving the disposable body from a first position spaced vertically below the heater to a second position in proximity to the heater prior to volatilizing the liquid with the heater.

18. The inhaler device according to claim 10, wherein the heater comprises a layer of resistance heating material on a substrate, the substrate including an opening located adjacent the outlet.

19. The inhaler device according to claim 18, wherein the layer of resistance heating material comprises a strip arranged in a pattern which is coextensive with the size of the chamber.

20. The inhaler device according to claim 19, wherein each of the aerosol generators includes a flow passage extending rectilinearly from the chamber, the heater including a first portion arranged to heat the chamber and a second portion arranged to heat the flow passage of a respective aerosol generator, the first and second portions of the heater comprising a layer of resistance heating material configured such that the second portion of the heater becomes hotter than the first portion of the heater during actuation of the heater to volatilize the liquid in the chamber.

21. The inhaler device according to claim 18, further comprising an opening device, the opening device being adapted to pierce at least one of the first layer and second layer and open the outlet.

22. The inhaler device according to claim 21, wherein the opening device includes a solenoid activated piercing element, the piercing element including a movable tip which is located in the opening in the substrate the tip being moved upon actuation of the piercing element such that the tip penetrates the first layer of the disposable body.

23. The inhaler device according to claim 9, wherein the disposable body is configured to fit in the inhaler device so as to allow advancement of each respective aerosol generator to a release position at which the heater can heat the liquid in the chamber of the respective aerosol generator.

24. The inhaler device according to claim 23, wherein the first layer comprises a layer of injection molded polymer material and the second layer of material comprises a foil heat sealed to the polymer layer, the inhaler device including an opening member which is operable to pierce the foil layer to open the outlet immediately prior to when the heater is activated to volatilize the liquid in the chamber.

25. The inhaler device according to claim 9, further comprising a dispensing member located adjacent the outlet of the aerosol generator, the vapor expelled from the opened outlet passing through a passage in the dispensing member.

26. The inhaler device according to claim 9, wherein the disposable body is movably supported such that the chamber can be moved to a release position at which the heater can heat the liquid in the chamber sufficiently to volatilize the liquid and expel the vapor through the opened outlet.

27. The inhaler device according to claim 21, wherein the opening device is fixedly attached to a portion of the inhale device and the inhaler device includes a lifting mechanism which moves the disposable body into engagement with the opening device so as to open the outlet.

28. The inhaler device according to claim 9, wherein the inhaler device comprises a housing and a cover, the cover being movable with respect to the housing so as to permit insertion of the disposable body in the inhaler device when the cover is in an open position.

29. The inhaler device according to claim 28, wherein the heater is mounted on a lower surface of the cover, the housing further including a lifting mechanism which moves the disposable body into engagement with an opening device so as to open the outlet of a respective aerosol generator.

30. The inhaler device according to claim 9, wherein the inhaler device includes a fluid delivery mechanism which engages the disposable body such that liquid in the chamber of a respective aerosol generator is forced out of the chamber, along a flow passage in the disposable body and toward the outlet, the heater being arranged to heat the liquid in the flow passage.

31. The inhaler device according to claim 30, wherein the fluid delivery mechanism includes a piston movable towards and away from the disposable body such that engagement of the disposable body with the piston forces liquid out of the chamber and into the flow passage at a substantially constant flow rate.

32. The inhaler device according to claim 31, wherein the inhaler device includes a driven piston cam which presses the piston against the disposable body, the piston cam being mounted on a shaft which is rotated by a motor when the motor is supplied power from a power source.

33. The inhaler device according to claim 32, further comprising a lifting mechanism which moves the disposable body into engagement with an opening device so as to form the outlet, the lifting device including a spindle received in an opening in the disposable body and spindle cam mounted on the shaft, the spindle cam pressing the spindle against the disposable body during rotation of the shaft.

34. The inhaler device according to claim 33, further comprising a gear wheel mounted on the shaft, the gear wheel engaging teeth on a outer periphery of the disposable body and effecting rotation of the disposable body upon rotation of the shaft.

35. The inhaler device according to claim 34, further comprising a controller operably connected to the motor, the power source and the heater so as to actuate the heater when liquid is forced out of the chamber by the piston.

36. The aerosol generator according to claim 1, wherein the sealed chamber of each of the aerosol generators comprises a reservoir in a lower surface of the disposable body and a flow passage in an upper surface of the disposable body, the flow passage being in fluid communication with the reservoir.

37. The aerosol generator according to claim 36, wherein a first layer of material on the lower surface covers the reservoir and a second layer of material on the upper surface covers the flow passage, the disposable body comprising a polymer material, the first layer of material comprising a polymer film and the second layer of material comprising a heat resistant material.

38. The aerosol generator according to claim 36, wherein the disposable body comprises gear teeth on an outer periphery thereof.

39. The aerosol generator according to claim 1, wherein the liquid includes a medicament selected from the group consisting of albuterol, isoproterenol sulfate, metaproterenol sulfate, terbutaline sulfate, pirbuterol acetate, salmeterol xinotoate, formotorol, beclomethasone dipropionate, flunisolide, fluticasone, budesonide, triamcinolone acetonide, beclomethasone dipropionate, triamcinolone acetonide, flunisolide, and fluticasone.

* * * * *